:

US007666410B2

(12) United States Patent
Lye et al.

(10) Patent No.: US 7,666,410 B2
(45) Date of Patent: Feb. 23, 2010

(54) DELIVERY SYSTEM FOR FUNCTIONAL COMPOUNDS

(75) Inventors: Jason Lye, Atlanta, GA (US); John Gavin MacDonald, Decatur, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 294 days.

(21) Appl. No.: 10/325,474

(22) Filed: Dec. 20, 2002

(65) Prior Publication Data

US 2004/0120904 A1    Jun. 24, 2004

(51) Int. Cl.
*A61K 35/00* (2006.01)
*A01N 25/34* (2006.01)
*A23K 1/17* (2006.01)
*A23K 1/165* (2006.01)
*C11D 3/39* (2006.01)

(52) U.S. Cl. .................. 424/123; 424/402; 424/442; 510/513

(58) Field of Classification Search .................. 424/489, 424/123, 402, 442
See application file for complete search history.

(56) References Cited

U.S. PATENT DOCUMENTS

| | | | |
|---|---|---|---|
| 2,015,864 A | 10/1935 | Müller et al. | |
| 2,593,146 A | 4/1952 | Howard | |
| 3,266,973 A | 8/1966 | Crowley | |
| 3,381,688 A | 5/1968 | Satas | |
| 3,507,269 A | 4/1970 | Berry | |
| 3,615,478 A | 10/1971 | Hoshino et al. | |
| 3,794,497 A | 2/1974 | Pratt et al. | |
| 3,919,437 A | 11/1975 | Brown et al. | |
| 3,960,494 A | 6/1976 | Verma et al. | |
| 4,038,046 A * | 7/1977 | Supkis ......................... | 51/295 |
| 4,041,203 A | 8/1977 | Brock et al. | |
| 4,172,781 A | 10/1979 | Walk et al. | |
| 4,297,233 A | 10/1981 | Gualandi | |
| RE30,797 E | 11/1981 | Davis | |
| RE30,803 E | 11/1981 | Davis | |
| 4,313,820 A | 2/1982 | Farha, Jr. et al. | |
| 4,325,735 A | 4/1982 | Ohta et al. | |
| 4,336,027 A | 6/1982 | Tussing | |
| 4,375,448 A | 3/1983 | Appel et al. | |
| 4,407,960 A | 10/1983 | Tratnyek | |
| 4,469,746 A | 9/1984 | Weisman et al. | |
| 4,488,969 A | 12/1984 | Hou | |
| 4,494,278 A | 1/1985 | Kroyer et al. | |
| 4,494,629 A | 1/1985 | Raeburn | |
| 4,517,308 A | 5/1985 | Ehlenz et al. | |
| 4,522,203 A | 6/1985 | Mays | |
| 4,525,410 A | 6/1985 | Hagiwara et al. | |
| 4,585,484 A | 4/1986 | Haruta et al. | |
| 4,640,810 A | 2/1987 | Laursen et al. | |
| 4,643,801 A | 2/1987 | Johnson | |
| 4,701,218 A | 10/1987 | Barker et al. | |
| 4,725,415 A | 2/1988 | Kidd | |
| 4,726,844 A | 2/1988 | Greenwood | |
| 4,734,324 A | 3/1988 | Hill | |
| 4,767,459 A | 8/1988 | Greenwood et al. | |
| 4,775,585 A | 10/1988 | Hagiwara | |
| 4,780,448 A | 10/1988 | Broecker et al. | |
| 4,783,220 A | 11/1988 | Gamble et al. | |
| 4,812,492 A | 3/1989 | Eckes et al. | |
| 4,818,464 A | 4/1989 | Lau | |
| 4,823,404 A | 4/1989 | Morell et al. | |
| 4,823,803 A | 4/1989 | Nakamura | |
| 4,836,851 A | 6/1989 | Pawlowski et al. | |
| 4,957,553 A | 9/1990 | Koike et al. | |
| 4,963,189 A | 10/1990 | Hindagolla | |
| 4,978,615 A | 12/1990 | Aoyama et al. | |
| 4,988,505 A | 1/1991 | Watanabe et al. | |
| 5,000,746 A | 3/1991 | Meiss | |
| 5,006,862 A | 4/1991 | Adamic | |
| 5,017,227 A | 5/1991 | Koike et al. | |
| 5,034,058 A | 7/1991 | Akiyama et al. | |
| 5,062,893 A | 11/1991 | Adamic et al. | |
| 5,064,694 A | 11/1991 | Gee | |
| 5,067,980 A | 11/1991 | Koike et al. | |

(Continued)

FOREIGN PATENT DOCUMENTS

EP        0232141 A1    8/1987

(Continued)

OTHER PUBLICATIONS

Ma et al, Adsorption of proteins and antibiotics onn poous alumina membranes, 1993, Studies in Surface Science and Catalysis, 80, 389-96.*
Ma et al, Studies in Surface Science and Catalysis, 1993, 80, 389-96.*
Haller, Dyes do not fast to ironing, Kolloid-Zeitschrift, 1926, 38, 248-253.*
Abstract of Article—*Non-hydrothermal synthesis of copper-,-zinc- and copper-zinc hydrosilicates*, T. M. Yurieva, G. N. Kustova, T. P. Minyukova, E. K. Poels, A. Bliek, M. P. Demeshkina, L. M. Plyasova, T. A. Krieger, and V. I. Zaikovskii, Materials Research Innovations, vol. 5, No. 1, Jun. 2001, pp. 3-11.
Article—*Adsorption of Gases in Multimolecular Layers*, Stephen Brunauer, P. H. Emmett, and Edward Teller, American Chemical Society, vol. 60, Jan.-Jun. 1938, pp. 309-319.

(Continued)

*Primary Examiner*—Alton N Pryor
(74) *Attorney, Agent, or Firm*—Dority & Manning, P.A.

(57) ABSTRACT

A delivery system for various functional compounds is disclosed. The delivery system incorporates a composition containing alumina. Various functional materials containing particular moieties may be adsorbed onto the alumina and used as desired. The functional compounds can be, for instance, pharmaceuticals, xenobiotics, anti-microbial agents, anti-viral agents, UV absorbers, odor control agents, fragrances, and the like. In one particular embodiment, for instance, certain dyes can be adsorbed onto the alumina surfaces. Once the dye is adsorbed onto the alumina surface, the resulting particles can be combined with a liquid vehicle for use in any suitable printing process.

45 Claims, No Drawings

U.S. PATENT DOCUMENTS

| | | |
|---|---|---|
| 5,069,719 A | 12/1991 | Ono |
| 5,091,004 A | 2/1992 | Tabayashi et al. |
| 5,092,926 A | 3/1992 | Owatari |
| 5,098,474 A | 3/1992 | Pawlowski et al. |
| 5,100,470 A | 3/1992 | Hindagolla et al. |
| 5,108,739 A | 4/1992 | Kurihara et al. |
| 5,122,418 A | 6/1992 | Nakane et al. |
| 5,133,803 A | 7/1992 | Moffatt |
| 5,145,518 A | 9/1992 | Winnik et al. |
| 5,145,727 A | 9/1992 | Potts et al. |
| 5,151,128 A | 9/1992 | Fukushima et al. |
| 5,156,675 A | 10/1992 | Breton et al. |
| 5,160,535 A | 11/1992 | Cooke et al. |
| 5,169,706 A | 12/1992 | Collier, IV et al. |
| 5,178,931 A | 1/1993 | Perkins et al. |
| 5,183,656 A | 2/1993 | Uesaka et al. |
| 5,188,885 A | 2/1993 | Timmons et al. |
| 5,190,581 A | 3/1993 | Fukushima et al. |
| 5,203,912 A | 4/1993 | Greenwood et al. |
| 5,204,111 A | 4/1993 | Handjani et al. |
| 5,204,429 A | 4/1993 | Kaminsky et al. |
| 5,209,998 A | 5/1993 | Kavassalis et al. |
| 5,220,346 A | 6/1993 | Carriera et al. |
| 5,221,332 A | 6/1993 | Kohlmeier |
| 5,223,026 A | 6/1993 | Schwartz, Jr. |
| 5,226,957 A | 7/1993 | Wickramanayake et al. |
| 5,230,732 A | 7/1993 | You et al. |
| 5,245,117 A | 9/1993 | Withers et al. |
| 5,258,065 A | 11/1993 | Fujisawa |
| 5,269,840 A | 12/1993 | Morris et al. |
| 5,274,025 A | 12/1993 | Stockle et al. |
| 5,300,365 A | 4/1994 | Ogale |
| 5,302,195 A | 4/1994 | Helbrecht et al. |
| 5,314,855 A | 5/1994 | Thorpe et al. |
| 5,340,929 A | 8/1994 | Ono et al. |
| 5,342,876 A | 8/1994 | Abe et al. |
| 5,344,872 A | 9/1994 | Debord et al. |
| 5,366,947 A | 11/1994 | Müller et al. |
| 5,370,730 A | 12/1994 | Gregory et al. |
| 5,382,283 A | 1/1995 | Yui et al. |
| 5,397,667 A | 3/1995 | Law et al. |
| 5,407,442 A | 4/1995 | Karapasha |
| 5,420,090 A | 5/1995 | Spencer et al. |
| 5,427,844 A | 6/1995 | Murai et al. |
| 5,431,723 A | 7/1995 | Bermes et al. |
| 5,439,514 A | 8/1995 | Kashiwazaki et al. |
| 5,441,561 A | 8/1995 | Chujo et al. |
| 5,451,450 A | 9/1995 | Erderly et al. |
| 5,472,775 A | 12/1995 | Obijeski et al. |
| 5,480,636 A | 1/1996 | Maruo et al. |
| 5,484,475 A | 1/1996 | Breton et al. |
| 5,486,356 A | 1/1996 | Yim |
| 5,487,938 A | 1/1996 | Spencer et al. |
| 5,512,095 A | 4/1996 | Sens et al. |
| 5,527,171 A | 6/1996 | Soerensen |
| 5,531,817 A | 7/1996 | Shields et al. |
| 5,538,548 A | 7/1996 | Yamazaki |
| 5,539,124 A | 7/1996 | Etherton et al. |
| 5,540,916 A | 7/1996 | Parks |
| 5,554,775 A | 9/1996 | Krishnamurti et al. |
| 5,565,022 A | 10/1996 | Wickramanayake |
| 5,580,655 A | 12/1996 | El-Shall et al. |
| 5,591,797 A | 1/1997 | Barthel et al. |
| 5,605,566 A | 2/1997 | Yui et al. |
| 5,616,315 A | 4/1997 | Masterman et al. |
| 5,626,654 A | 5/1997 | Breton et al. |
| 5,626,655 A | 5/1997 | Pawlowski et al. |
| 5,633,109 A | 5/1997 | Jennings et al. |
| 5,656,072 A | 8/1997 | Kato et al. |
| 5,661,197 A | 8/1997 | Villiger et al. |
| 5,663,224 A | 9/1997 | Emmons et al. |
| 5,667,572 A | 9/1997 | Taniguch et al. |
| 5,679,138 A | 10/1997 | Bishop et al. |
| 5,679,724 A | 10/1997 | Sacripante et al. |
| 5,681,380 A | 10/1997 | Nohr et al. |
| 5,684,063 A | 11/1997 | Patel et al. |
| 5,693,126 A | 12/1997 | Ito |
| 5,695,868 A | 12/1997 | McCormack |
| 5,725,643 A | 3/1998 | Higashiyama |
| 5,733,272 A | 3/1998 | Brunner et al. |
| 5,747,003 A | 5/1998 | Mohnot et al. |
| 5,749,951 A | 5/1998 | Yoshiike et al. |
| 5,753,026 A | 5/1998 | Kuntz et al. |
| 5,756,561 A | 5/1998 | Wang et al. |
| 5,769,931 A | 6/1998 | Wang et al. |
| 5,777,639 A | 7/1998 | Kageyama et al. |
| 5,785,745 A | 7/1998 | Lauw et al. |
| 5,788,749 A | 8/1998 | Breton et al. |
| 5,788,753 A | 8/1998 | Pawlowski et al. |
| 5,795,985 A | 8/1998 | Hüsler et al. |
| 5,810,917 A | 9/1998 | Yamazaki et al. |
| 5,814,685 A | 9/1998 | Satake et al. |
| 5,817,300 A | 10/1998 | Cook et al. |
| 5,833,744 A | 11/1998 | Breton et al. |
| 5,837,352 A | 11/1998 | English et al. |
| 5,843,509 A | 12/1998 | Calvo Salve et al. |
| 5,852,073 A | 12/1998 | Villiger et al. |
| 5,855,660 A | 1/1999 | Bujard et al. |
| 5,858,503 A | 1/1999 | Everhart et al. |
| 5,861,144 A | 1/1999 | Peterson et al. |
| 5,868,823 A | 2/1999 | Yamazaki et al. |
| 5,871,872 A * | 2/1999 | Matijevic et al. ............... 430/7 |
| 5,874,067 A | 2/1999 | Lucas et al. |
| 5,879,439 A | 3/1999 | Nagai et al. |
| 5,880,176 A | 3/1999 | Kamoto et al. |
| 5,882,391 A | 3/1999 | Gregory et al. |
| 5,882,392 A | 3/1999 | Gregory et al. |
| 5,882,638 A | 3/1999 | Dodd et al. |
| 5,885,599 A | 3/1999 | Peterson et al. |
| 5,888,286 A | 3/1999 | Gregory et al. |
| 5,891,230 A | 4/1999 | Gregory et al. |
| 5,891,232 A | 4/1999 | Moffatt et al. |
| 5,891,934 A | 4/1999 | Moffatt et al. |
| 5,897,541 A | 4/1999 | Uitenbroek et al. |
| 5,911,816 A | 6/1999 | Gore |
| 5,916,596 A | 6/1999 | Desai et al. |
| 5,928,416 A | 7/1999 | Gundlach et al. |
| 5,928,419 A | 7/1999 | Uemura et al. |
| 5,935,309 A | 8/1999 | Moffatt et al. |
| 5,935,310 A | 8/1999 | Engel et al. |
| 5,942,027 A | 8/1999 | Ikai et al. |
| 5,944,883 A | 8/1999 | Saibara et al. |
| 5,948,155 A | 9/1999 | Yui et al. |
| 5,948,398 A | 9/1999 | Hanamoto et al. |
| 5,948,483 A | 9/1999 | Kim et al. |
| 5,955,515 A | 9/1999 | Kimura et al. |
| 5,958,998 A | 9/1999 | Foucher et al. |
| 5,962,566 A | 10/1999 | Grandfils et al. |
| 5,964,926 A | 10/1999 | Cohen |
| 5,964,930 A | 10/1999 | Saibara et al. |
| 5,968,244 A | 10/1999 | Ueda et al. |
| 5,972,389 A | 10/1999 | Shell et al. |
| 5,973,025 A | 10/1999 | Nigam et al. |
| 5,973,027 A | 10/1999 | Howald et al. |
| 5,980,623 A | 11/1999 | Hiraoka et al. |
| 5,981,623 A | 11/1999 | McCain et al. |
| 5,989,510 A | 11/1999 | Abe et al. |
| 5,993,527 A | 11/1999 | Tochihara et al. |
| 5,993,856 A | 11/1999 | Ragavan et al. |
| 5,998,222 A | 12/1999 | Weimer |
| 6,004,625 A | 12/1999 | Oshima |
| 6,015,454 A | 1/2000 | Lacroix et al. |
| 6,015,455 A | 1/2000 | Yano et al. |
| 6,019,827 A | 2/2000 | Wickramanayake et al. |

| | | | |
|---|---|---|---|
| 6,024,785 A | 2/2000 | Morimoto | |
| 6,024,786 A | 2/2000 | Gore | |
| 6,025,412 A | 2/2000 | Sacripante et al. | |
| 6,033,463 A | 3/2000 | Yui et al. | |
| 6,034,154 A | 3/2000 | Kase et al. | |
| 6,037,391 A | 3/2000 | Iida | |
| 6,045,606 A | 4/2000 | Matzinger | |
| 6,045,900 A | 4/2000 | Haffner et al. | |
| 6,047,413 A | 4/2000 | Welchel et al. | |
| 6,048,390 A | 4/2000 | Yano et al. | |
| 6,051,057 A | 4/2000 | Yatake et al. | |
| 6,060,410 A | 5/2000 | Gillberg-LaForce et al. | |
| 6,073,771 A | 6/2000 | Pressley et al. | |
| 6,075,179 A | 6/2000 | McCormack et al. | |
| 6,090,193 A | 7/2000 | Nigam et al. | |
| 6,096,299 A | 8/2000 | Guarracino et al. | |
| 6,099,627 A | 8/2000 | Saibara et al. | |
| 6,110,266 A | 8/2000 | Gonzalez-Blanco et al. | |
| 6,111,163 A | 8/2000 | McCormack et al. | |
| 6,113,680 A | 9/2000 | Aoyama et al. | |
| 6,121,365 A | 9/2000 | Saibara et al. | |
| 6,129,786 A | 10/2000 | Camara et al. | |
| 6,140,390 A | 10/2000 | Bugner et al. | |
| 6,147,139 A | 11/2000 | Shaw-Klein et al. | |
| 6,149,719 A | 11/2000 | Houle | |
| 6,153,001 A | 11/2000 | Suzuki et al. | |
| 6,159,649 A | 12/2000 | Macholdt et al. | |
| 6,165,440 A | 12/2000 | Esenaliev | |
| 6,171,382 B1 | 1/2001 | Stübbe et al. | |
| 6,172,173 B1 | 1/2001 | Spencer et al. | |
| 6,177,608 B1 | 1/2001 | Weinstrauch | |
| 6,190,814 B1 | 2/2001 | Law et al. | |
| 6,193,844 B1 | 2/2001 | McLaughlin et al. | |
| 6,200,555 B1 | 3/2001 | Nishijima et al. | |
| 6,210,625 B1 | 4/2001 | Matsushita et al. | |
| 6,238,767 B1 | 5/2001 | McCormack et al. | |
| 6,254,894 B1 | 7/2001 | Denkewicz, Jr. et al. | |
| 6,264,615 B1 | 7/2001 | Diamond et al. | |
| 6,277,346 B1 | 8/2001 | Murasawa et al. | |
| 6,277,489 B1 | 8/2001 | Abbott et al. | |
| 6,277,772 B1 | 8/2001 | Gancet et al. | |
| 6,294,222 B1 | 9/2001 | Cohen et al. | |
| 6,299,867 B1 | 10/2001 | Aoyagi et al. | |
| 6,309,736 B1 | 10/2001 | McCormack et al. | |
| 6,344,218 B1 | 2/2002 | Dodd et al. | |
| 6,344,272 B1 | 2/2002 | Oldenburg et al. | |
| 6,358,537 B1 | 3/2002 | Hoshino et al. | |
| 6,358,909 B1 | 3/2002 | Ochomogo et al. | |
| 6,361,780 B1 | 3/2002 | Ley et al. | |
| 6,369,290 B1 | 4/2002 | Glaug et al. | |
| 6,376,741 B1 | 4/2002 | Guarracino et al. | |
| 6,410,765 B1 | 6/2002 | Wellinghoff et al. | |
| 6,425,530 B1 | 7/2002 | Coakley | |
| 6,428,814 B1 | 8/2002 | Boash et al. | |
| 6,432,872 B1 | 8/2002 | Tsushio et al. | |
| 6,460,989 B1 | 10/2002 | Yano et al. | |
| 6,467,897 B1 | 10/2002 | Wu et al. | |
| 6,475,601 B1 | 11/2002 | Sakaki et al. | |
| 6,479,150 B1 | 11/2002 | Liu et al. | |
| 6,486,227 B2 | 11/2002 | Nohr et al. | |
| 6,491,790 B1 | 12/2002 | Proverb et al. | |
| 6,498,000 B2 | 12/2002 | Murasawa et al. | |
| 6,517,199 B1 | 2/2003 | Tomioka et al. | |
| 6,531,704 B2 | 3/2003 | Yadav et al. | |
| 6,536,890 B1 | 3/2003 | Kato et al. | |
| 6,548,264 B1 | 4/2003 | Tan et al. | |
| 6,551,457 B2 | 4/2003 | Westman et al. | |
| 6,575,383 B2 | 6/2003 | Dobler et al. | |
| 6,578,521 B2 | 6/2003 | Raymond et al. | |
| 6,589,562 B1 | 7/2003 | Shefer et al. | |
| 6,607,711 B2 | 8/2003 | Pedersen | |
| 6,623,848 B2 | 9/2003 | Brehm et al. | |
| 6,638,918 B2 | 10/2003 | Davison et al. | |
| 6,639,004 B2 | 10/2003 | Falat et al. |
| 6,645,569 B2 | 11/2003 | Cramer et al. |
| 6,693,071 B2 | 2/2004 | Ghosh et al. |
| 6,780,896 B2 | 8/2004 | MacDonald et al. |
| 7,008,979 B2 | 3/2006 | Schottman et al. |
| 2001/0000889 A1 | 5/2001 | Yadav et al. |
| 2001/0023338 A1 | 9/2001 | Guarracino et al. |
| 2001/0031248 A1 | 10/2001 | Hall-Puzio et al. |
| 2001/0056246 A1 | 12/2001 | Rodriguez-Fernandez |
| 2002/0005145 A1 | 1/2002 | Sherman |
| 2002/0066542 A1 | 6/2002 | Jakob et al. |
| 2002/0091071 A1 | 7/2002 | Fischer et al. |
| 2002/0106466 A1 | 8/2002 | Hausmann et al. |
| 2002/0110686 A1 | 8/2002 | Dugan |
| 2002/0128336 A1 | 9/2002 | Kolb |
| 2002/0142937 A1 | 10/2002 | Carter et al. |
| 2002/0149656 A1 | 10/2002 | Nohr |
| 2002/0150678 A1 | 10/2002 | Cramer et al. |
| 2002/0176982 A1 | 11/2002 | Rohrbaugh et al. |
| 2002/0177621 A1 | 11/2002 | Hanada |
| 2002/0182102 A1 | 12/2002 | Fontenot et al. |
| 2003/0013369 A1 | 1/2003 | Soane et al. |
| 2003/0021983 A1 | 1/2003 | Nohr et al. |
| 2003/0050211 A1 | 3/2003 | Hage et al. |
| 2003/0056648 A1 | 3/2003 | Fornai et al. |
| 2003/0070782 A1 | 4/2003 | Proverb et al. |
| 2003/0082237 A1 | 5/2003 | Cha et al. |
| 2003/0099718 A1 | 5/2003 | Burrell et al. |
| 2003/0100842 A1 | 5/2003 | Rosenberg et al. |
| 2003/0147956 A1 | 8/2003 | Shefer et al. |
| 2003/0147966 A1 | 8/2003 | Franzen et al. |
| 2003/0181540 A1 | 9/2003 | Quellet et al. |
| 2003/0203009 A1 | 10/2003 | MacDonald |
| 2003/0235605 A1 | 12/2003 | Lelah et al. |
| 2004/0033269 A1 | 2/2004 | Hei et al. |
| 2004/0034157 A1 | 2/2004 | Ghosh et al. |
| 2004/0043688 A1 | 3/2004 | Soerens et al. |
| 2004/0120921 A1 | 6/2004 | Quincy, III et al. |
| 2004/0122387 A1 | 6/2004 | Long et al. |

FOREIGN PATENT DOCUMENTS

| | | |
|---|---|---|
| EP | 0251783 B1 | 1/1988 |
| EP | 0282287 B2 | 9/1988 |
| EP | 0348978 A2 | 1/1990 |
| EP | 0376448 B1 | 7/1990 |
| EP | 0389015 A2 | 9/1990 |
| EP | 0389015 A3 | 9/1990 |
| EP | 0389023 A2 | 9/1990 |
| EP | 0389023 A3 | 9/1990 |
| EP | 0483500 A1 | 5/1992 |
| EP | 0510619 A1 | 10/1992 |
| EP | 0749295 B1 | 12/1996 |
| EP | 0972563 A1 | 1/2000 |
| EP | 1034800 A1 | 9/2000 |
| EP | 1157672 A1 | 11/2001 |
| EP | 1162172 A1 | 12/2001 |
| EP | 1188854 A1 | 3/2002 |
| EP | 1214878 A1 | 6/2002 |
| EP | 1216675 A1 | 6/2002 |
| EP | 1298071 A1 | 4/2003 |
| EP | 1315526 B1 | 6/2003 |
| EP | 1053788 B1 | 10/2003 |
| JP | 55017157 * | 5/1980 |
| JP | 62149322 | 7/1987 |
| JP | 3221142 | 9/1991 |
| WO | WO 8902698 A1 | 4/1989 |
| WO | WO 9111977 A1 | 8/1991 |
| WO | WO 9112029 A1 | 8/1991 |
| WO | WO 9112030 A1 | 8/1991 |
| WO | WO 9619346 A2 | 6/1996 |
| WO | WO 9619346 A3 | 6/1996 |
| WO | WO 9725076 A1 | 7/1997 |

| | | | |
|---|---|---|---|
| WO | WO 9814524 A1 | 4/1998 | |
| WO | WO 9820915 A1 | 5/1998 | |
| WO | WO 9826808 A2 | 6/1998 | |
| WO | WO 9826808 A3 | 6/1998 | |
| WO | WO 9947252 A2 | 3/1999 | |
| WO | WO 9947253 A1 | 3/1999 | |
| WO | WO 9947252 A3 | 9/1999 | |
| WO | WO 0003797 A1 | 1/2000 | |
| WO | WO 0029036 A2 | 3/2000 | |
| WO | WO 0029036 A3 | 3/2000 | |
| WO | WO 00137764 | 3/2000 | |
| WO | WO 0059555 A1 | 10/2000 | |
| WO | WO 0066090 A1 | 11/2000 | |
| WO | WO 0076558 A1 | 12/2000 | |
| WO | WO-01/06054 | * | 1/2001 |
| WO | WO 0106045 A1 | 1/2001 | |
| WO | WO 0106054 A1 | 1/2001 | |
| WO | WO 0202347 A1 | 1/2002 | |
| WO | WO 0226272 A1 | 4/2002 | |
| WO | WO 0249559 A2 | 6/2002 | |
| WO | WO 02055115 A1 | 7/2002 | |
| WO | WO 02062881 A2 | 8/2002 | |
| WO | WO 02064877 A2 | 8/2002 | |
| WO | WO 02064877 A3 | 8/2002 | |
| WO | WO 02083297 A1 | 10/2002 | |
| WO | WO 02084017 A1 | 10/2002 | |
| WO | WO 02094329 A1 | 11/2002 | |
| WO | WO 02095112 A1 | 11/2002 | |
| WO | WO 03000979 A2 | 1/2003 | |
| WO | WO 03025067 A1 | 3/2003 | |
| WO | WO 03032959 A1 | 4/2003 | |
| WO | WO 03051278 A2 | 6/2003 | |
| WO | WO 03051278 A3 | 6/2003 | |
| WO | WO 03088931 A2 | 10/2003 | |
| WO | WO 03092885 A1 | 11/2003 | |
| WO | WO 2004060378 A2 | 7/2004 | |

OTHER PUBLICATIONS

Article—*Study of the urea thermal decomposition (pyrolysis) reaction and importance to cyanuric acid production*, Peter M. Schaber, James Colson, Steven Higgins, Ed Dietz, Daniel Thielen, Bill Anspach, and Jonathan Brauer, American Laboratory, Aug. 1999, pp. 13-21.
Abstract of Japanese Patent No. JP1262868, Oct. 19, 1989.
Abstract of Japanese Patent No. JP2157039, Jun. 15, 1990.
Abstract of Japanese Patent No. JP3195562, Aug. 27, 1991.
Abstract of Japanese Patent No. JP4335141, Nov. 24, 1992.
Abstract of Japanese Patent No. JP5261246, Oct. 12, 1993.
Abstract of Japanese Patent No. JP6285140, Oct. 11, 1994.
Abstract of Japanese Patent No. JP63072337, Apr. 2, 1988.
Abstract of Japanese Patent No. JP8152409, Jun. 11, 1996.
Abstract of SU834073, May 30, 1981.
PCT Search Report and Written Opinion for PCT/US2004/011596, Aug. 30, 2004.
PCT Search Report and Written Opinion for PCT/US2004/016933, Nov. 2, 2004.
Abstract of Japanese Patent No. JP04255767, Sep. 10, 1992.
Abstract of Japanese Patent No. JP05098185, Apr. 20, 1993.
Article—*Immunization of mice with peptomers covalently couopled to aluminum oxide nanoparticles*, Andreas Frey, Nicholas Mantis, Pamela A. Kozlowski, Alison J. Quayle, Adriana Bajardi, Juana J. Perdomo, Frank A. Robey, and Marian R. Neutra, Vaccine, vol. 17, 1999, pp. 3007-3019.
PCT Search Report for PCT/US03/39737, Jun. 18, 2004.
PCT Search Report for PCT/US03/32846, Jun. 7, 2004.
Abstract of Japanese Patent No. 7256025, Oct. 9, 1995.
Abstract of Japanese Patent No. 5106199, Apr. 27, 1993.
Abstract of Japanese Patent No. 9143872, Jun. 3, 1997.
Article—*Applicability of a SPME method for the Rapid Determination of VOCs*, Alexandre Béné, Jean-Luc Luisier, and Antoine Fornage, Chimia, vol. 56, No. 6, 2002, pp. 289-291.

Article—*Characterisation of novel modified active carbons and marine algal biomass for the selective adsorption of lead*, D.J. Malik, V. Strelko, Jr., M. Streat, and A.M. Puziy, Water Research, vol. 36, 2002, pp. 1527-1538.
Article—*Significance of Ammonia in the Genesis of Gastric Epithelial Lesions Induced by Helicobacter pylori: An in vitro Study with Different Bacterial Strains and Urea Concentrations*, P. Sommi, V. Ricci, R. Fiocca, M. Romano, K.J. Ivey, E. Cova, E. Solcia, and U. Ventura, Digestion, vol. 57, 1996, pp. 299-304.
Article—*Ammonia vapour in the mouth as a diagnostic marker for Helicobacter pylori infection: preliminary "proof of principle" pharmacological investigations*, C. D. R. Dunn, M. Black, D. C., Cowell, C. Penault, N. M. Ratcliffe, R. Spence, and C. Teare, British Journal of Biomedical Science, vol. 58, 2001, pp. 66-76.
Article—*Purification and Characterization of Urease from Helicobacter pylori*, Bruce E. Dunn, Gail P. Campbell, Guillermo I. Perez-Perez, and Martin J. Blaser, The Journal of Biological Chemistry, vol. 265, No. 16, Jun. 5, 1990, pp. 9464-1990.
Article—*Validation of $^{13}C$-Urea Breath Test for the Diagnosis of Helicobacter pylori Infection in the Singapore Population*, T. S. Chua, K. M. Fock, E. K. Teo, T. M. Ng, Singapore Medical Journal, vol. 43, No. 8, 2002, pp. 408-411.
Article—*Significance of ammonia produced by Helicobacter pylori*, Shigeji Ito, Yoshihiro Kohli, Takuji Kato, Yoshimichi Abe, and Takashi Ueda, European Journal of Gastroenterology & Hepatology, vol. 6, No. 2, 1994, pp. 167-174.
Article—*Spectrophotometric Assay of Thiols*, Peter C. Jocelyn, Methods in Enzymology, vol. 142, 1987, pp. 44-67.
Article—*Adsorption of Dyes on Nanosize Modified Silica Particles*, Guangwei Wu, Athanasia Koliadima, Yie-Shein Her, and Egon Matijevic, Journal of Colloid and Interface Sciences, vol. 195, 1997, pp. 222-228.
Article—*Adsorption of Proteins and Antibiotics on Porous Alumina Membranes*, Yi Hua Ma, Aseem Bansal, and William M. Clark, Fundamentals of Adsorption, vol. 80, 1992, pp. 389-396.
Product Information on Snowtex®, 6 pages.
Abstract of Japanese Patent JP2000129179, May 9, 2000.
Abstract of Japanese Patent JP8259868, Oct. 8, 1996.
Abstract of Japanese Patent JP63105078, May 10, 1988.
Abstract of Japanese Patent JP56143272, Nov. 7, 1981.
Article—*Uniform Deposition of Ultrathin Polymer Films on the Surfaces of $Al_2O_3$ Nanoparticles by a Plasma Treatment*, Donglu Shi, S. X. Want, Jim J. van Ooij, L. M. Wang, Jiangang Zhao, and Zhou Yu, Jun. 2000, 15 pages.
Article—*Development of Novel Dye-Doped Silica Nanoparticles for Biomarker Application*, Swadeshmukul Santra, Kemin Wang, Rovelyn Tapec, and Weihong Tan, Journal of Biomedical Optics, vol. 6, No. 2, Apr. 2001, pp. 160-166.
Article—*Nanoparticles Based on Polyelectrolyte Complexes: Effect of Structure and Net Charge on the Sorption Capability for Solved Organic Molecules*, H. M. Buchhammer, G. Petzold, and K. Lunkwitz, Colloid Polym. Sci., vol. 278, No. 9, Sep. 2000, pp. 841-847.
Article—*Industrial Organic Pigments*, W. Herbst and K. Hunger, 1997, 6 pages.
Product Information—Aldrich, 2000-2001, 4 pages.
Abstracts of Papers, $221^{st}$ ACS National Meeting, San Diego, CA, Apr. 1-5, 2000.
Article—*Adsorption and Encapsulation of Fluorescent Probes in Nanoparticles*, Olga V. Makarova, Agnes E. Ostafin, Hirokazu Miyoshi, and James R. Norris, Jr., The Journal of Physical Chemistry B®, vol. 103, No. 43, Oct. 28, 1999, pp. 9080-9084.
Article—*UV Excimer Radiation from Dielectric-Barrier Discharges*, B. Eliasson and U. Kogelschatz, Applied Physics B, vol. B 46, No. 4, Aug. 1988, pp. 299-303.
Article—*Silent Discharges for the Generation of Ultraviolet and Vacuum Ultraviolet Excimer Radiation*, Ulrich Kogelschatz, Pure and Applied Chemistry, vol. 62, No. 9, 1990, pp. 1667-1674.

* cited by examiner

DELIVERY SYSTEM FOR FUNCTIONAL COMPOUNDS

BACKGROUND OF THE INVENTION

A delivery system generally refers to a system that aids or otherwise facilitates the delivery of a functional material to a desired location. The functional material can be any material that acts upon a substrate or otherwise provides a benefit once delivered to the desired location. Examples of functional materials that may benefit from the use of a delivery system include pharmaceuticals that are intended to be ingested or subcutaneously injected into a patient, fragrances, vitamins and nutrients, and various other and numerous additives.

In one particular application, for instance, the functional material can be a dye that is intended to be printed or otherwise applied to a substrate. In the past, various delivery systems for dyes have been proposed that are intended to facilitate application of the dye to a substrate, such as a textile material. The delivery systems, for instance, are intended to affix the dye to a substrate, prevent the dye from fading when exposed to sunlight, to prevent the dye from degrading when exposed to the environment, to facilitate application of the dye to the substrate, or, for example, to render the dye more stable.

Even in view of recent advances in the art, further improvements in delivery systems for functional materials are still needed. For example, a need currently exists for a delivery system that can bind to various functional materials that does not incorporate relatively expensive chemical formulations or that does not require any complex process steps for incorporating a functional material into the delivery system. With respect to dyes, a need also exists in the art for a delivery system for a dye that is capable of affixing the dye to negatively charged surfaces. For example, a need currently exists for a delivery system for dyes that is capable of affixing the dyes to textile materials containing natural or synthetic polymeric fibers that have a negative surface charge.

SUMMARY OF THE INVENTION

The present invention is generally directed to a delivery system for various functional materials. The functional materials can be, for instance, colorants, UV absorbers, pharmaceuticals, odor control agents, fragrances, anti-microbial agents, anti-viral agents, antibiotics, xenobiotics, nutriceutical agents, and the like. In accordance with the present invention, the functional materials are adsorbed onto alumina that is contained in a particle. The resulting particle can then be used as is or can be combined with a vehicle, such as a liquid vehicle, to deliver the functional material to a desired location. For example, when the functional material is a colorant, the particles of the present invention can be incorporated into a liquid vehicle and applied to a substrate using any conventional printing means.

Thus, in one embodiment, the present invention is directed to a particle containing alumina. At least a portion of the alumina contained within the particle is present on a surface of the particle. A functional compound is bonded to the alumina on the surface of the particle. The functional compound prior to bonding with the alumina contains a moiety comprising:

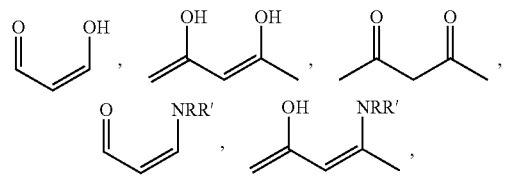

a tautomer thereof, or a functional equivalent thereof and wherein R and R' comprise independently hydrogen, an alkyl group, or an aryl group.

The above moieties can be present as is on a functional compound. Alternatively, however, each of the above moieties can include further R groups attached to the carbon chain shown above. In general, any such R group can appear in association with the above moieties as long as the R group does not interfere with the bonding of the moiety to an alumina.

The above moieties have been found to form a bond with alumina in constructing the compositions of the present invention. Of particular significance, it was discovered that the functional compound, in some embodiments, can bond with alumina without significantly changing the positive charge character of alumina. For example, under certain conditions, alumina may have a positive surface charge. It has been discovered that even after the functional material is bonded to the alumina, the resulting structure still maintains a positive charge. Thus, in one embodiment of the present invention, positively charged particles are formed. Due to their positive charge, the particles may be securely affixed to the surface of a substrate that carries with it a negative charge through coulombic attraction.

In one particular embodiment of the present invention, novel recording mediums, inks, and nanoparticles containing a colorant compound may be formed. In accordance with the present invention, such recording mediums, when applied to substrates, exhibit improved water and detergent resistance. For example, the delivery system of the present invention can improve the durability performance of the recording mediums especially to substrates having a negative charge. For instance, in one embodiment, a recording medium such as an ink-jet ink, can be produced according to the present invention that is substantive to substrates containing synthetic polymeric fibers, such as polypropylene fibers, polyethylene fibers, polyester fibers, and the like.

Other features and aspects of the present invention are discussed in greater detail.

DETAILED DESCRIPTION

It is to be understood by one of ordinary skill in the art that the present discussion is a description of exemplary embodiments only, and is not intended as limiting the broader aspects of the present invention, which broader aspects are embodied in the exemplary construction.

In general, the present invention is directed to a delivery system for functional compounds. Functional compounds can be any suitable substance that can provide a benefit to a location once delivered. In accordance with the present invention, the delivery system is generally directed to the construction of a particle containing alumina. The alumina contained within the particle provides a bonding site on the surface of the particle for a functional compound. Specifically, the functional compound becomes adsorbed onto the surface of the alumina. Once the functional compound is bonded to the alumina, the resulting particle can then be used to deliver the functional compound to a particular location. The particles can be used as is, for instance, or can be combined with a liquid vehicle which may facilitate delivery of the particles depending upon the particular application.

Functional compounds that are well suited for use in the present invention include compounds that contain at least one of the following moieties:

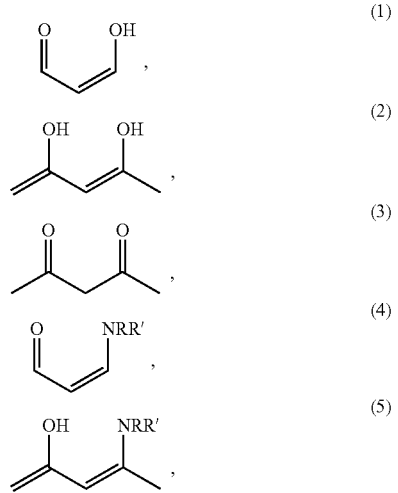

a tautomer thereof, or a functional equivalent thereof and wherein R and R' comprise independently hydrogen, an alkyl group, or an aryl group. As used herein, a functional equivalent to one of the above moieties refers to functional materials that include similar reactive groups as shown above, but which are not positioned on a molecule as exactly shown above and yet will still bond with alumina in a similar manner.

Referring to the moieties shown above, moiety (1) may be considered a carboxy-hydroxy moiety. Moiety (2) may be considered a hyrdoxy-hydroxy moiety, while moiety (3) may be considered a carboxy-carboxy moiety. Moieties (4) and (5), on the other hand, can be considered vinylalogous amide moieties. In moieties (4) and (5) above, the amine groups can be primary amines, secondary amines, or tertiary amines. In general, any suitable functional compound containing one of the above moieties or a functional equivalent thereof may be used in accordance with the present invention. Further, it should be understood that various additional R groups may be included with the above moieties as long as the R groups do not interfere with the bond that is formed with alumina.

The present inventors have discovered that the above moieties may form a relatively strong bond to an alumina surface. The functional compounds may be bonded to the alumina surface in order to change the properties of the resulting particle or to perform a particular function. Without wishing to be bound by theory, it is believed that the above moieties form a bidentate ligand bonding system with alumina surfaces. For instance, it is believed that alumina forms a covalent bond and a coordinate bond with the above moieties. Further, it is believed that a surface reaction occurs causing the functional compound to remain on the surface of the particle and form a coating thereon. The functional material can cover the entire resulting particle or can be located at particular locations on the particle. Further, it should be understood that the particles of the present invention can contain more than one functional compound.

Of particular advantage, in many embodiments, it has also been discovered that a functional compound can be bonded to alumina without significantly impacting on the positive surface charge of alumina, which can be measured as zeta potential. The term "zeta potential" is used herein to mean without limitation a potential gradient that arises across an interface. This term especially refers to the potential gradient that arises across the interface between the boundary layer in contact with the particle of the present invention and the diffuse layer surrounding the particle. Zeta potential measurements can be taken using, for instance, a Zetapals instrument which are available from the Brookhaven Instrument Corporation of Holtsville, N.Y. For example, zeta potential measurements can be conducted by adding one to three drops of a sample into a cuvet containing 1 mM KCl solution, using the instrument's default functions preset for aqueous solutions.

Thus, once alumina is bonded to the functional material, the resulting molecule continues to maintain a relatively strong positive charge. For instance, particles made according to the present invention can have a zeta potential of greater than 20 mV, particularly greater than 30 mV, and, in some embodiments, greater than 40 mV. By remaining positively charged, the particles are well suited for being affixed to substrates that carry a negative surface charge through coulombic attraction. Depending upon the difference in charge between the particle of the present invention and the surface of a substrate, the bond in some applications can be relatively permanent and substantive. Consequently, the delivery system of the present invention can be used to affix functional compounds to various substrates without the use of chemical binders or other attachment structures.

Various different particles and compositions can be used in the present invention that contain alumina. For example, in one embodiment, the functional material is combined with an alumina sol. Many different types of alumina sols are commercially available with varying particle size. Of particular advantage, alumina sols can be prepared that carry a relatively strong positive surface charge or zeta potential. In this embodiment, the particle that is reacted with the functional compound contains primarily and in some embodiments exclusively alumina.

In other embodiments, however, the particle reacted with the functional compound can contain various other ingredients. In general, the particle can contain any material that does not adversely interfere with ability of the functional material to bond to alumina. In this regard, at least a portion of the alumina contained within the particle should be present on the surface of the particle so that the alumina is available for adsorbing the functional compound.

In one particular embodiment of the present invention, the particle can contain a core material coated with alumina. The alumina can form a continuous coating over the particle or a discontinuous coating. The core material can be, for instance, an inorganic oxide, such as silica. For example, in one embodiment, sols can be used that contain silica nanoparticles that have an alumina surface coating. Such sols are currently commercially available, for instance, from Nissan Chemical America of Houston, Tex. The silica is coated with alumina to provide stability to the sols over certain pH ranges. In fact, alumina coated silica sols may have greater stability in some applications of the present invention in comparison to alumina sols.

As described above, any suitable functional compound containing one of the above moieties, a tautomer thereof, or a functional equivalent thereof may be used in accordance with the present invention. Examples of functional compounds include pharmaceuticals, and xenobiotics. Xenobiotics is a general term used to describe any chemical interacting with an organism that does not occur in the normal metabolic pathways of that organism. Other functional compounds can include UV absorbers, odor control agents, fragrances, therapeutic agents, nutriceutical agents, anti-viral agents, anti-microbial agents, and the like. One example of a therapeutic agent that may be used in the present invention is hydrocortisone. Examples of nutriceutical agents include ascorbic acid and aspartame. In one particular embodiment, the functional compound may be tetracycline, which is a known antibacterial agent.

In still another embodiment of the present invention, the functional compound can be a colorant, such as dye. Particular examples of dyes that may be used in accordance with the present invention are discussed in greater detail below.

Once any of the above-mentioned functional compounds are bound to alumina, the alumina acts as a delivery vehicle for delivering the functional compound to a desired location. Once bound to the alumina, the functional compounds may be easier to handle, may be more stable, or may have other improved properties depending upon the application. Further, the resulting alumina structure can be incorporated into various other mediums. For instance, the alumina structure can be incorporated into liquid vehicles, can be formed into capsules, can be combined with gels, pastes, other solid materials, and the like.

The particles formed according to the present invention containing alumina and the functional compound can be present in various forms, shapes, and sizes depending upon the desired result. For instance, the particles can be of any shape, for example, a sphere, a crystal, a rod, a disk, a tube, or a string of particles. The size of the particle can also vary dramatically. For instance, in one embodiment, the particles can have an average dimension of less than about 1 mm, particularly less than about 500 microns, and more particularly less than about 100 microns. In other embodiments, however, even smaller sizes may be desired. For instance, the particles can have an average diameter of less than about 1,000 nm, and particularly less than about 500 nm. As used herein, the average dimension of a particle refers to the average length, width, height, or diameter of a particle.

As described above, the particles of the present invention include a surface layer that contains one or more functional compounds. The coating on the particle can be continuous or discontinuous. The particle itself is amorphous.

In one particular embodiment, the present invention is directed to a delivery system for dyes. In particular, it has been discovered that the use of alumina as described above provides various advantages and benefits when attempting to apply a dye to a substrate. For instance, it has been discovered that the alumina delivery system can provide a means to make permanent prints onto substrates having negatively charged surfaces, such as substrates containing thermoplastic polymers as well as natural fibers. The ink becomes affixed to the substrate at relatively low cost and low complexity without the use of chemical binders and without the use of a pre-treatment or post-treatment process on the substrate.

For example, once a dye is adsorbed onto alumina in accordance with the present invention, for many applications, the resulting particle has a positive charge. Thus, the particle can be affixed to negatively charged surfaces through coulombic attraction. Depending upon the charge difference between the particles and the substrate, the dye may exhibit permanent properties such as wash fastness by being resilient to water and detergents. For example, generally wash fastness can be obtained if the charge difference between the substrate and the particle is greater than about 42 mV.

In general, any dye containing a carbonyl-hydroxy moiety, a hydroxy-hydroxy moiety, a carbonyl-carbonyl moiety, a vinylalagous amide moiety, a tautomer thereof, or a functional equivalent thereof as described above may be used in the process of the present invention. Various examples of dyes that may be adsorbed onto alumina are as follows. It should be understood, however, that the below list is not exhaustive and is not intended as limiting the invention.

Dyes Containing the Anthraquinone (5) Chromophore

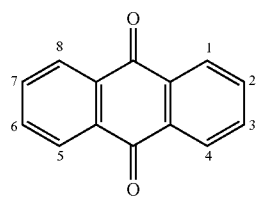

5

Numbers indicate the substitution positions of the anthraquinone structure. This table indicates dye substituents that occur at positions 1, 4, 5, or 8 on the anthraquinone structure. In other words, this table shows the presence of groups that form alumina bonding moieties 1 through 5.

| Name | Substituent at position 1 or 4 or 5 or 8 | Other groups present include |
|---|---|---|
| CI Acid Black 48 | NH2 | SO3Na |
| CI Acid Blue 25 | NH2 | SO3Na |
| CI Acid Blue 40 | NH2 | SO3Na |
| CI Acid Blue 41 | NH2 | SO3Na |
| CI Acid Blue 45 | OH, NH2 | SO3Na |
| CI Acid Blue 129 | NH2 | SO3Na |
| CI Acid Green 25 | NHAr | SO3Na |
| CI Acid Green 27 | NHAr | SO3Na |
| CI Acid Green 41 | OH, NHAr | SO3Na |
| CI Mordant Red 11 (Alizarin) | OH | |
| CI Mordant Black 13 (Alizarin Blue Black B) | OH, NHAr | SO3Na |
| Alizarin Complexone (Aldrich 12,765-5) | OH | |
| CI Mordant Red 3 (Alizarin Red S) | OH | SO3Na |
| CI Natural Red 4 (Carminic Acid) | OH | COOH |
| CI Disperse Blue 1 | NH2 | |
| CI Disperse Blue 3 | NH(alkyl) | |
| CI Disperse Blue 14 | NHCH3 | |
| Emodin (6-methyl-1,3,8-trihydroxy anthraquinone) | OH | |
| Nuclear Fast Red (Heliofast Rubine BBL) | OH, NH2 | SO3Na |
| CI Natural Red 16 (Purpurin) | OH | |
| CI Natural Red 8 | OH | |
| Quinalizarin | OH | |
| Quinizarin | OH | |
| CI Reactive Blue 2 | NH2, NHAr | SO3Na |
| Solvent Green 3 | NHAr | |

Dyes Containing Salicylate, or 3-hydroxy-2-naphthoic Acid Moieties

Dyes containing salicylate (6, R=OH), Salicamide (6, R=NH2, NHAr, NHAlk), or BON acid (3-hydroxy-2-naphthoic acid) (7, R=OH) or a nitrogenous BON acid derivative (7, R=NH2, NHAr, NHAlk) moiety as shown below may also be used in accordance with the present invention. These dyes often fall into the Colour Index Mordant application class.

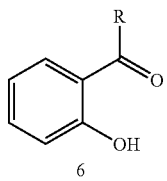 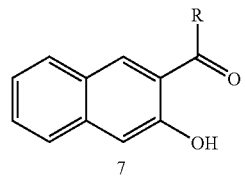

| Colorant | Substantive Group | Chromophore |
| --- | --- | --- |
| Aluminon (tri ammonium salt) (Aurintricarboxylic acid) (CI Mordant Violet 39 is the trisodium salt) | Salicylate | TPM |
| CI Mordant Blue 29 | Salicylate | TPM |
| CI Mordant Blue 3 (Chromoxane Cyanine R) | Salicylate | TPM |
| Calconcarboxylic acid 3-hydroxy-4-(2-hydroxy-4-sulfo-1-naphthylazo)-2-naphthalenecarboxylic acid | BON acid | Azo |
| CI Mordant Orange 1 (Alizarin Yellow R) | Salicylate | Azo |
| CI Mordant Orange 6 (Chrome Orange GR) | Salicylate | Azo |
| CI Mordant Orange 10 | Salicylate | Azo |
| CI Mordant Yellow 7 | Salicylate | Azo |
| CI Mordant Yellow 10 | Salicylate | Azo |
| CI Mordant Yellow 12 | Salicylate | Azo |
| CI Mordant Green 31 (Naphtho Chrome Green) | BON Acid | Azo |
| CI Azoic Coupling Component 2 (Naphthol AS) | Arylamido BON acid | N/A |
| CI Azoic Coupling Component 45 (Naphthol AS B1) | Arylamido BON acid | N/A |
| 3-hydroxy-2-naphthoic acid (BON Acid) | BON Acid | N/A |
| Xylidyl Blue 1 | Aryl amido BON acid | Azo |

Dyes Based Upon Chromotropic Acid

Dyes based upon Chromotropic acid 8 are also substantive to alumina. Azo dyes are formed when chromotropic acid is reacted with a diazonium salt. Azo coupling occurs at positions 2 and/or 7.

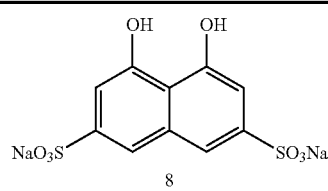

| Colorant |
| --- |
| CI Acid Red 176 (Chromotrope 2B) |

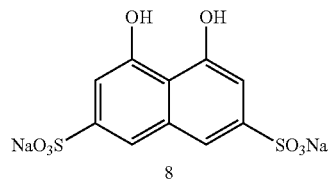

| Colorant |
| --- |
| CI Acid Red 29 (Chromotrope 2R) |
| Plasmocorinth B |
| Sulfonazo III |
| (3,6-Bis(2-sulfophenylazo)-4,5-dihydroxy-2,7-naphthalene disulfonic acid sodium salt) |
| 2-(4-sulfophenylazo)-1,8-dihydroxy-3,6-naphthalenedisulfonic acid |

Dyes Containing Acetoacetanilide

Dyes containing acetoacetanilide moieties 9 also contain the correct geometry to bond to alumina. Azo dyes couple to acetoacetanilide beta to the two carboxyl groups. An example is CI Acid Yellow 99, 10. Acetoacetanilide will adsorb onto the surface of alumina.

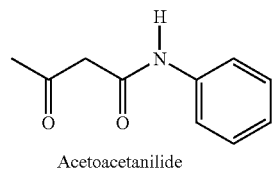

Acetoacetanilide

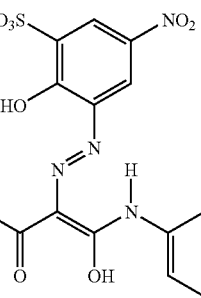

CI Acid Yellow 99

Naphthoquinone Colorants

Naphthoquinone (11) type Structures are also useful for forming complexes with the surface of alumina:

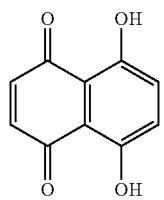

CI Natural Black 1 (Hematoxylin) is another example of a dye that contains quinoid groups and is substantive to alumina.

Aluminum Dyes; Dyes Known to be Useful for Staining Anodized Aluminum

There are several dyes that are know to be useful for the coloration of anodized aluminum, including CI Mordant Red 7 (Eriochrome Red B), 12. It is believed that the geometry of the five membered pyrazolone ring oxygen atom brings it into the correct position with the beta-naphthol group for complexation with alumina. Thus, the following structure can be considered a functional equivalent to a carbonyl-hydroxy moiety. The structure also contains an iminalogous amide moiety, which is functionally equivalent to a vinalogous amide.

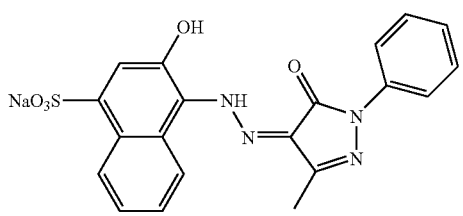

Aluminum Lake Forming Dyes

Certain anionic dyes may be precipitated using certain metal ions to form an insoluble colored compounds know as Lake Pigments. For example, Erythrosine (Tetraiodofluorescein) forms an insoluble salt with aluminum ions. The salt is known as CI Pigment Red 172.

CI Pigment Blue 36 is the aluminum lake of indigo disulfonate (FD+C Blue 1):

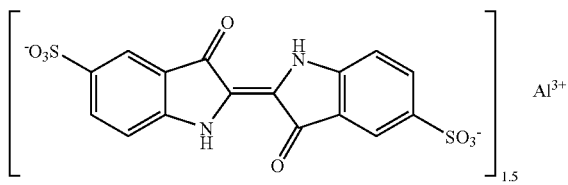

In addition to a dye as described above, in some embodiments, it may be desirable to bond other functional compounds or additives to the alumina. For instance, additives that assist in the dyeing process or that stabilize the dye may also be bonded to the alumina if the additive contains a moiety as described above. Such functional additives that may be used include charge carriers, thermal oxidation stabilizers, crosslinking agents, plasticizers, a charge control additive, a flow control additive, a filler, a surfactant, a chelating agent, a colorant stabilizer, or a combination thereof.

Various methods can be utilized to construct dye particles in accordance with the present invention that contain a dye adsorbed onto alumina. For instance, in some applications, the alumina and the dye containing a reactive moiety can be combined and reacted in an aqueous solution.

In some embodiments, however, the dye may be difficult to dissolve in water. In this embodiment, the dye can first be dissolved in a minimum quantity of a solvent. The solvent can be, for instance, acetone, ethanol or a similar liquid that is miscible with water. After the dye is combined with the solvent, if desired, a surfactant can be added in an amount greater than about 0% to about 50% by weight of dye solids added. In general, the amount of surfactant added to the solvent should be minimized. One suitable surfactant that can be used, for instance, is SURFYNOL 440 surfactant sold by Air Products and Chemicals, Inc. located in Allentown, Pa.

With rapid stirring, the dissolved dye solution can then be added to a dilute aqueous suspension that contains particles comprising alumina. Although not critical, better results may be achieved if the aqueous suspension is slightly heated.

After constant stirring for a sufficient amount of time, the dye disperses by precipitation throughout the mixture and slowly dissolves into the water. Once dissolved into the water, the dye can be adsorbed by the alumina contained in the particles.

Once the dye is adsorbed onto the alumina, the resulting particles can be used to formulate a suitable colorant composition for use in various processes, such as in a suitable printing process.

The colorant composition may comprise an aqueous or non-aqueous medium, although an aqueous medium is useful for applications which employ liquid printing mediums. The colorant compositions of the present invention contain particles, as well as, desirable colorant stabilizers and additives. For example, the colorant composition may contain the above-described particles in combination with any of the following additives: a second colorant; a colorant stabilizer, such as a porphine; a molecular includant; a pre-polymer; and any additional components as described above.

The present invention encompasses recording mediums such as ink jet inks comprising the nanoparticles disclosed herein. Inks used in ink jet printers are described in U.S. Pat. No. 5,681,380, assigned to Kimberly-Clark Worldwide, Inc., which is incorporated herein by reference in its entirety. Ink jet inks will usually contain water as the principal solvent, preferably deionized water in a range of between about 20 to about 95 percent by weight, various co-solvents in an amount of between about 0.5 and about 20 percent by weight, and the particles of the present invention.

Various co-solvents may also be included in the ink formulation. Examples of such co-solvents include a lactam such as N-methyl pyrrolidone. However, other examples of optional co-solvents include N-methylacetamide, N-methylmorpholine-N-oxide, N,N-dimethylacetamide, N-methyl formamide, propyleneglycolmonomethylether, tetramethylene sulfone, and tripropyleneglycolmonomethylether. Still other solvents which may be used include propylene glycol and triethanolamine (TEA). If an acetamide-based cosolvent is also included in the formulation it is typically present at about 5 percent by weight, within a range of between about 1.0-12 percent by weight.

Optionally, one or more humectants in an amount between about 0.5 and 20 percent by weight may be included in the ink formula. Additional humectants for optional use in the formulation include, but are not limited to, ethylene glycol, diethylene glycol, glycerine, and polyethylene glycol 200, 400, and 600, propane 1,3 diol, other glycols, a propyleneglycolmonomethyl ether, such as Dowanol PM (Gallade Chemical Inc., Santa Ana, Calif.), polyhydric alcohols, or combinations thereof.

Other additives may also be included to improve ink performance, such as a chelating agent to sequester metal ions that could become involved in chemical reactions that could spoil the ink over time, for example for use with metal complex dyes, a corrosion inhibitor to help protect metal components of the printer or ink delivery system, a biocide or biostat to control unwanted bacterial, fungal, or yeast growth in the ink, and a surfactant to adjust the ink surface tension. However, the use of a surfactant may be dependent on the type of printhead to be used. If a surfactant is included, it is typically present in an amount of between about 0.1 to about 1.0 percent by weight. If a corrosion inhibitor is included, it is typically present in an amount between about 0.1 and about 1.0 percent by weight. If a biocide or biostat is included, it is typically present in an amount between about 0.1 and about 0.5 percent by weight.

If a biocide or biostat is added to the ink formulation, it may be exemplified by Proxel GXL (Zeneca Corporation, Wilmington, Del.). Other examples include Bioban DXN (Angus Chemical Company, Buffalo Grove, Ill.). If a corrosion inhibitor is added to the formulation, it may be exemplified by Cobratec (PMC Specialty Group Distributing of Cincinnati, Ohio). Alternate corrosion inhibitors include sodium nitrite, triethanolamine phosphate, and n-acyl sarcosine. Still other examples include benzotriazole (Aldrich Chemical Company, Milwaukee, Wis.). If a surfactant is included in the formulation, it is typically a nonionic surfactant exemplified by Surfynol 504 (Air Products and Chemicals, Inc., Allentown, Pa.). Still other examples include Surfynol 465, and Dynol 6.04 also available from Air Products. If a chelating agent is included in the formulation it may be exemplified by an ethylene diaminetetraacetic acid (EDTA). Other additives such as pH stabilizers/buffers, (such as citric acid and acetic acid as well as alkali metal salts derived therefrom), viscosity modifiers, and defoaming agents such as Surfynol DF-65, may also be included in the formulation, depending on the product application.

Depending upon how the colorant composition is formulated, the composition can be used in various printing processes. For instance, in addition to ink jet printing and other non-impact printers, the colorant composition can be used in screen printing processes, offset lithographic processes, flexographic printing processes, rotogravure printing processes, and the like. In some of the above printing processes, a thickener may need to be added to the colorant composition. The thickener can be, for instance, an alginate.

The recording medium or colorant composition of the present invention may be applied to any substrate to impart a color to the substrate. The substrate to which the composition is applied may include, but is not limited to, paper, wood, a wood product or composite, woven fabrics, non-woven fabrics, textiles, films, plastics, glass, metal, human skin, animal skin, leather and the like. In one aspect, the colorant composition or recording medium may be applied to textile articles such as clothing.

In one particular embodiment, a colorant composition containing particles of the present invention may be applied to a substrate having a negative surface charge. As described above, the alumina contained in the particles of the present invention retain a positive charge even after adsorption of a dye. Consequently, the particles remain affixed to negatively charged surfaces. In fact, wash durability of the colorant composition may occur if there is a substantial amount of charge difference between the substrate and the particles of the present invention.

In view of the above, colorant compositions made according to the present invention are particularly well suited to being applied to natural and synthetic substrates that have a negative surface charge. For instance, naturally occurring materials that generally contain a negative surface charge include cotton fibers, cellulose fibers, and substrates made therefrom. Such substrates include all types of fabrics, garments and apparel, paper products, and the like.

In addition to the above natural materials, in one particular embodiment, colorant compositions made according to the present invention have been found to be well suited to being applied to substrates made from synthetic polymers, such as thermoplastic polymers. Such substrates can include, for instance, woven and non-woven materials made from a polyolefin polymer such as polypropylene or polyethylene, polyester, and the like. In the past, various problems have been experienced in trying to affix dyes to these types of materials. Consequently, either complicated dye structures have been used or dyes and or pigments have been applied in conjunction with chemical binders. The particles of the present invention, however, can permanently affix to these materials without the use of chemical binders or complex chemical constructions.

Although not needed, in some embodiments it may be desirable to pre-treat or post-treat the polymer substrates which may further serve to affix the dyes to the materials. For instance, substrates made from synthetic polymers can undergo a pretreatment process for increasing the negative surface charge. For example, such pretreatment processes include subjecting the substrate to a corona treatment or to an electret treatment. An electret treatment, for instance, is disclosed in U.S. Pat. No. 5,964,926 to Cohen, which is incorporated herein by reference in its entirety. Such pretreatments have been found not only to increase the negative surface charge of polymeric materials, but also assist in wetting out the polymer and enhancing surface adhesion between the polymer and the particles of the present invention.

In addition to pretreatment processes, substrates contacted with the particles of the present invention can also undergo various post treatment processes which further serve to affix the particles to the substrate. For example, in one embodiment, the treated substrate can be subjected to radio frequency radiation or to microwave radiation. Alumina is known to adsorb radio frequency radiation and microwave radiation causing the particles to heat. Once heated, it is believed that the particles become further embedded into the polymeric substrate. Further, the particles can be heated without also heating the substrate to higher than desired temperatures.

The present invention may be better understood with respect to the following examples.

EXAMPLE 1

Aluminasol 200 (Nissan Chemical America) was diluted with DI water to give a 2% Aluminasol 200 suspension. Meanwhile, carminic acid (0.02 g) was suspended in DI water (1 g). Carminic acid includes hydroxy-carbonyl moieties and can be represented as follows:

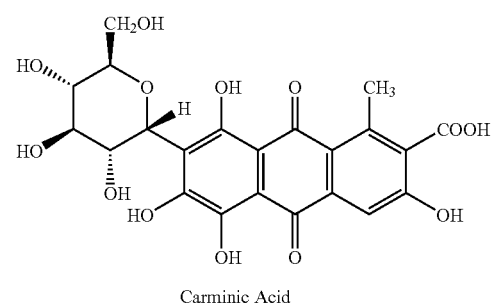

Carminic Acid

The zeta potential of alumina particles in the Aluminasol was monitored as carminic acid was dripped into the measurement cell. The zeta potential did not change as more carminic acid was added. A significant color shift was observed as the carminic acid (red/orange) was added to the Aluminasol (bluish magenta). The following zeta potential results were obtained:

|  | Zeta Potential |
|---|---|
| 2% Aluminasol | 56.70 mV |
| Aluminasol + 2 Drops Carminic | 49.27 mV |
| Aluminasol + 5 drops carminic | 56.68 mV |
| Aluminasol + 7 drops carminic | 58.59 mV |

As shown above, the positively charged alumina was capable of adsorbing carminic acid without going through a charge reversal step.

EXAMPLE 2

Aluminasol 200 (Nissan Chemical America, 2 g) was diluted with DI water (98 g) with good stirring. Carminic acid (Aldrich, #22,925-3) (0.5011 g) was suspended in DI water (23.7135 g) with good stirring. The carminic acid did not dissolve completely at this concentration, and so whenever portions were taken, they were taken while stirring vigorously so that suspended solids were also withdrawn. A hypodermic syringe was used to withdraw 1 ml of carminic acid suspension. This was added to the diluted Aluminasol 200 with good stirring. The suspension changed from a white to a bluish red.

The Zeta potential was monitored after addition to check for changes as follows:

|  | Zeta Potential |
|---|---|
| Initial (2% Aluminasol) | +55.70 mV |
| 2 min after carminic acid addition | +45.08 mV |
| 5 min after carminic acid addition | +45.68 mV |

This mixture was allowed to stir overnight. The next morning, all dye had dissolved, and no dye crystals were observed.

EXAMPLE 3

In this example, in addition to carminic acid, CI Acid Blue 25 and CI Acid Blue 45 were bonded to alumina in accordance with the present invention. CI Acid Blue 25 and CI Acid Blue 45 have the following structures:

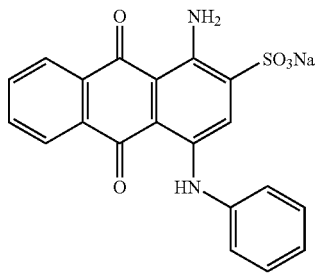

CI Acid Blue 25

0.2008 g CI Acid Blue 25 (Aldrich) was added to 19.7735 g DI water and stirred to give a suspension, which was stirred for 30 minutes. 1 ml of this was added to a mixture containing 2 g Aluminasol and 98 g DI water. Mixture stirred overnight to ensure that all dye had dissolved.

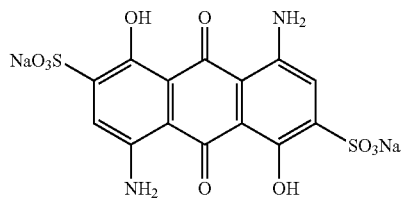

CI Acid Blue 45

0.2507 g of CI Acid Blue 45 (Aldrich) was suspended in 20.1751 g DI water with stirring for 30 minutes. 1 ml (syringe) was added to a mixture of 2 g Aluminasol and 98 g of DI water to give a blue complex. Mixture stirred overnight to ensure that all dye dissolved.

In the following sample, a high concentration of Aluminasol 200 was combined with carminic acid. Specifically, 0.111 g glacial acetic acid (Fischer, ACS plus reagent grade) was diluted with 29.795 g DI water. This was added to 49.941 g of Aluminasol 200, slowly with good stirring. This mixture was stirred for 20 mins, at which point, 4 ml (measured using a syringe) of a suspension of carminic acid in DI water (0.5011 g carminic acid in 23.7135 g water) was added at once, with good stirring. Mixture stirred overnight.

A fourth sample was then constructed containing the same ingredients (carminic acid) in the same amounts as listed in Example 2 above.

All mixtures appeared to be homogeneous in that upon standing for three hours, no sludge settled out, and no dark dye crystals were observed. Zeta potentials and particle size analysis were conducted using a Brookhaven Instrument PALS Zeta potential analyzer for all the samples except the sample containing CI Acid Blue 25. The following results were obtained:

| System | Zeta Potential | Mean Diameter | Half Distribution Width |
|---|---|---|---|
| 2% Aluminasol/Acid Blue 45 | +40.69 mV | 333.5 nm | 94.7 nm |
| 2% Aluminasol/Carminic Acid | +45.14 mV | 300.6 nm | 139.5 nm |
| 50% Aluminasol/Carminic Acid | +43.73 mV | 347.3 nm | 181.6 nm |

The above three solutions were then subjected to a dialysis test to demonstrate that the dye was adsorbed onto the alumina surfaces. Specifically, the three solutions were dialyzed against 3% glacial acetic acid using Sigma Dialysis Tubing (Cellulose, 12,000 mw cut off, Sigma D-0655. Tubing was soaked in DI water for two hours prior to use to remove glycerine, and to make the tubing flexible.) As a control, a small amount of carminic acid was added to a dialysis tubing and placed in a bath containing 3% acetic acid. Within 2 hours, carminic acid had traversed the cellulose membrane and had colored the 3% acetic acid solution. No color was observed from the aluminasol mixtures, suggesting, along with the color change, that the colorant was strongly sorbed by the particles. The next morning, the 50% aluminasol/carminic acid solution had colored the water bluish red. However, it is believed that the bag had ruptured. Also, a very faint, almost indiscernible blue coloration was noticed in the dialysis solution of the aluminasol acid blue 45 dialysis, suggesting that this colorant did not as strongly adsorb into the alumina.

EXAMPLE 4

The following tests were conducted to demonstrate the washfastness of the particles of the present invention on cotton.

The three compositions prepared in Example 3 above containing 2% aluminasol/Acid Blue 45; 2% aluminasol/carminic acid, and 50% aluminasol/carminic acid were spotted onto cotton poplin fabric (0.01198 g/cm², from Yuhan-Kimberly, uncoated) and dried overnight at 60° C. As the aluminasol containing mixtures were dropped onto the cotton, it was observed that only the flooded area of the fabric took up color. Colorless water wicked out from around the spotted area suggesting that i) no unadsorbed dye was present in the mixture, and ii) the nanoparticles sorbed onto the cotton, and were immobilized.

A control sample was also prepared. In particular, a carminic acid solution was first formulated containing 0.5011 grams of carminic acid in 23.7135 grams of DI water. The carminic acid solution was dropped onto cotton poplin fabric using a pipette and allowed to dry overnight at 60° C.

Samples were washed by i) rinsing under a hot running tap, and then by stirring for 2 hours in 2 liters of water containing 1 g/liter Aerosol OT (dioctyl sodium sulfosuccinate surfactant obtained from Cytec Industries of West Patterson, N.J.) and 1 g/liter of sodium bicarbonate, with stirring (mechanical paddle stirrer). Samples were entered into the washing bath at 60° C., and the bath cooled over two hours to 30° C. The fabric was rinsed in cold water, then dried in the air at ambient.

The Carminic acid of the control sample rinsed out of the cotton. Almost all of the dye/Aluminasol complex remained as a bluish-red stain.

EXAMPLE 5

The following tests were conducted to demonstrate the washfastness of particles made according to the present invention on a polypropylene non-woven spunbond fabric. The spunbond fabric tested had a basis weight of 2 osy.

Polypropylene spunbond was smeared with i) carminic acid, ii) the concentrated 50% Aluminasol/carminic acid complex suspension prepared in Example 3 and iii) the 2% Aluminasol/carminic acid complex suspension prepared in Example 3. In all cases, the polypropylene was difficult to wet out with these materials, and so smearing was required using a rubber-gloved finger and the teat pipette used to apply the liquids. Once the material had been smeared on forcibly, the material showed little retraction. The samples were allowed to dry overnight at 60° C.

More polypropylene was smeared with the 50% Aluminasol/carminic acid complex. These samples were dried at 60° C. and then cut in half. Half of the samples were subjected to microwave radiation (Sharp carousel domestic microwave oven, model #R-410 CK, output 1100 Watt) for a range of times. (10 seconds, 20 seconds, 28 seconds)

All polypropylene samples were washed using the same procedure as for the cotton in Example 4 above. The following results were obtained:
i) Carminic acid of the control sample rinsed out of the PP.
ii) Some, but not all of the aluminasol/carminic acid inks were retained on the polypropylene. The nature of the washing out was not a general fading of the area. However, there appeared to be a loss of all material from certain areas, but not others. In other words, it looked as though the ink had not wet out the polypropylene.
iii) Considerably more aluminasol/carminic acid was retained on samples that were microwaved prior to washing. It is thought that the microwave treatment may have heated the colored particles, allowing them to embed in the polypropylene. Microwaving for longer time did not considerably improve the washfastness of the prints.

EXAMPLE 6

In this example, instead of using an alumina sol, a sol containing silica particles that had an alumina surface coating were used. The surface coated silica suspension was obtained from Nissan Chemical America of Houston, Tex. The suspension is sold under the trade name SNOWTEX-AK.

50 ml of 20% wt/wt suspension of SNOWTEX-AK (Nissan Chemical America, Houston, Tex.) was stirred at ambient temperature while 0.2 grams of carminic acid dye (Aldrich Chemical Company, Milwaukee, Wis.) was added. Stirring was continued overnight and resulted in a dramatic color change from blood red to blue/purple.

The physical parameters of the nanoparticles are:

| | |
|---|---|
| SNOWTEX-AK | Size: 62 nm and Zeta Potential: +36 mV. |
| SNOWTEX-AK with carminic acid | Size: 83 nm and Zeta Potential: +35 mV. |

The bond formation of the aluminum-dye complex did not result in a change in zeta potential.

The above "ink" solution was applied to 4"×4" pieces of untreated cotton fabric and allowed to air-dry. A similar control sample was constructed using only carminic acid. The dried fabrics were then subjected to a washing cycle in 2 liters of water containing Ajax liquid detergent and sodium bicarbonate at 60° C. for 2 hours. The fabric samples were then air-dried. The SNOWTEX-AK/carminic acid sample did not loose any color after the washing cycle. In contrast, the control sample (a sample stained with 0.2 g Carminic Acid in 50 ml water, dried under the same conditions) lost all of the color upon washing under the same conditions.

EXAMPLE 7

The following example demonstrates the application of the present invention to other functional compounds as opposed to dyes.

Tetracycline is an antibacterial agent that contains a carbonyl-hydroxy function capable of bonding with alumina in accordance with the present invention. Tetracycline is a series of isomers of cyclomycin. Tetracycline contains as a principle component the following:

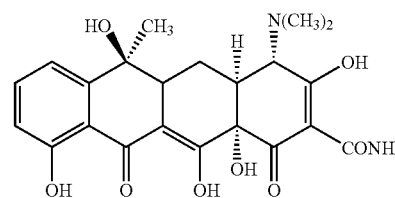

4S-(4,4,5,6,12)-4-(dimethylamino)-1,4,4,5,5,6,11,12-octahydro-3,6,10,12,12-pentahydroxy-6-methyl-1, 11-dioxo-2-naphthacenecarboxamide.

The UV-visible absorbance spectrum of Tetracycline was measured using a UV-visible spectrophotometer (Perkin-Elmer UV-Visible spectrophotometer.) Tetracycline was found to absorb at 357 nm in water. When SNOWTEX AK suspension (as described in Example 6) was added to the tetracycline solution, a bathochromic shift occurred to give an absorbance of 365 nm, suggesting that the tetracycline had adsorbed onto the alumina surface of SNOWTEX AK particles.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed:

1. An article of manufacture comprising:
   a nonwoven material having a receiving surface containing negative charges, wherein the nonwoven material comprises polyolefin fibers; and
   a plurality of positively charged particles bonded to the receiving surface of the nonwoven material through coulombic attraction, the particles containing silica coated with alumina, at least a portion of the alumina being present on a surface of the particles, and wherein a functional compound is bonded to the alumina on the surface of the particle, the functional compound prior to bonding with the alumina containing a moiety comprising:

[chemical structures]

or a tautomer thereof, or a functional equivalent thereof and wherein R and R' comprise independently hydrogen, an alkyl group, or an aryl group.

2. An article as defined in claim 1, wherein the functional compound comprises a colorant, a UV absorber, a pharmaceutical, an odor control agent, a fragrance, a therapeutic agent, a nutriceutical agent, an anti-bacterial agent, an antimicrobial agent, an anti-viral agent, a xenobiotic, or combinations thereof.

3. An article as defined in claim 1, wherein the particle containing alumina bonded to the functional compound has an average dimension of less than 1 mm.

4. An article as defined in claim 1, wherein the particle containing alumina bonded to the functional compound has an average dimension of less than 1,000 nm.

5. An article as defined in claim 1, wherein the functional compound comprises hydrocortisone, ascorbic acid, or aspartame.

6. An article as defined in claim 1, wherein the functional compound comprises tetracycline.

7. An article as defined in claim 1, wherein the particle containing alumina bonded to the functional compound has a zeta potential of at least 20 mV.

8. An article as defined in claim 1, wherein the plurality of particles are contained within a liquid vehicle when applied to the nonwoven material.

9. An article as defined in claim 1, wherein the functional compound comprises a dye.

10. An article as defined in claim 1, wherein the nonwoven material is subjected to a corona treatment prior to bonding with the plurality of positively charges particles.

11. An article as defined in claim 1, wherein the nonwoven material is subjected to an electret treatment prior to bonding with the plurality of positively charges particles.

12. An article as defined in claim 1, wherein the article has been exposed to microwave radiation or radio frequency radiation after the nonwoven material and the plurality of charged particles have been bonded together.

13. An article as defined in claim 9, wherein the dye contains an anthraquinone chromophore.

14. An article as defined in claim 9, wherein the dye contains salicylate or 3-hydroxy-2-naphthoic acid moieties.

15. An article as defined in claim 9, wherein the dye is based on chromotropic acid.

16. An article as defined in claim 9, wherein the dye contains an acetoacetanilide.

17. An article as defined in claim 9, wherein the dye contains a naphthoquinone.

18. An article as defined in claim 9, wherein the dye contains the moiety:

[chemical structure with O and OH]

or a tautomer of this moiety.

19. An article as defined in claim 9, wherein the dye contains the moiety:

[chemical structure with O and NRR']

and wherein R and R' are hydrogen.

20. An article as defined in claim 9, wherein the dye contains the moiety:

[chemical structure with OH and OH]

or a tautomer of this moiety.

21. An article as defined in claim 9, wherein the plurality of particles have an average dimension of less than 1,000 nm.

22. An article as defined in claim 1, wherein the receiving surface of the nonwoven material and the particles have a surface charge difference of at least 42 mV.

23. An article as defined in claim 1, wherein the receiving surface of the nonwoven material and the particles have a surface charge difference of at least 42 mV.

24. An article of manufacture comprising:
a nonwoven spunbond fabric having a receiving surface containing negative charges, wherein the spunbond fabric comprises polyolefin fibers; and
a plurality of positively charged particles bonded to the receiving surface of the spunbond web through coulombic attraction, the particles containing silica coated with alumina, at least a portion of the alumina being present on a surface of the particles, and wherein a functional compound is bonded to the alumina on the surface of the particle, the functional compound prior to bonding with the alumina containing a moiety comprising:

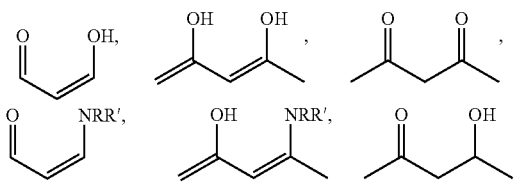

or a tautomer thereof, or a functional equivalent thereof and wherein R and R' comprise independently hydrogen, an alkyl group, or an aryl group.

25. An article as defined in claim 24, wherein the particle comprises a core material coated with alumina.

26. An article as defined in claim 25, wherein the core material comprises silica.

27. An article as defined in claim 24, wherein the functional compound comprises a colorant, a UV absorber, a pharmaceutical, an odor control agent, a fragrance, a therapeutic agent, a nutriceutical agent, an anti-bacterial agent, an anti-microbial agent, an anti-viral agent, a xenobiotic, or combinations thereof.

28. An article as defined in claim 24, wherein the particle containing alumina bonded to the functional compound has an average dimension of less than 1 mm.

29. An article as defined in claim 24, wherein the particle containing alumina bonded to the functional compound has an average dimension of less than 1,000 nm.

30. An article as defined in claim 24, wherein the functional compound comprises hydrocortisone, ascorbic acid, or aspartame.

31. An article as defined in claim 24, wherein the functional compound comprises tetracycline.

32. An article as defined in claim 24, wherein the particle containing alumina bonded to the functional compound has a zeta potential of at least 20 mV.

33. An article as defined in claim 24, wherein the plurality of particles are contained within a liquid vehicle when applied to the spunbond fabric.

34. An article as defined in claim 24, wherein the functional compound comprises a dye.

35. An article as defined in claim 34, wherein the dye contains an anthraquinone chromophore.

36. An article as defined in claim 34, wherein the dye contains salicylate or 3-hydroxy-2-naphthoic acid moieties.

37. An article as defined in claim 34, wherein the dye is based on chromotropic acid.

38. An article as defined in claim 34, wherein the dye contains an acetoacetanilide.

39. An article as defined in claim 34, wherein the dye contains a naphthoquinone.

40. An article as defined in claim 34, wherein the dye contains the moiety:

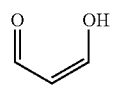

or a tautomer of this moiety.

41. An article as defined in claim 34, wherein the dye contains the moiety:

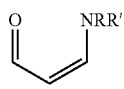

and wherein R and R' are hydrogen.

42. An article as defined in claim 34, wherein the dye contains the moiety:

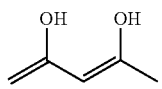

or a tautomer of this moiety.

43. An article as defined in claim 24, wherein the plurality of particles have an average dimension of less than 1,000 nm.

44. An article as defined in claim 24, wherein the receiving surface of the spunbond fabric and the particles have a surface charge difference of at least 42 mV.

45. An article as defined in claim 24, wherein the receiving surface of the spunbond fabric and the particles have a surface charge difference of at least 42 mV.

* * * * *

UNITED STATES PATENT AND TRADEMARK OFFICE
CERTIFICATE OF CORRECTION

PATENT NO.       : 7,666,410 B2                                              Page 1 of 1
APPLICATION NO.  : 10/325474
DATED            : February 23, 2010
INVENTOR(S)      : Lye et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 194 days.

Signed and Sealed this

Seventh Day of December, 2010

David J. Kappos
*Director of the United States Patent and Trademark Office*